United States Patent [19]

Toda et al.

[11] Patent Number: 4,777,042

[45] Date of Patent: Oct. 11, 1988

[54] CHOLESTEROL LEVEL-LOWERING AGENTS

[75] Inventors: Hideo Toda; Kunio Kihara; Susumu Mizogami; Munehiro Hashimoto, all of Ami, Japan

[73] Assignees: Mitsubishi Petrochemical Co., LTd.; Mitsubishi Chemical Industries Ltd., both of Tokyo, Japan

[21] Appl. No.: 102,767

[22] Filed: Sep. 25, 1987

Related U.S. Application Data

[63] Continuation of Ser. No. 718,074, Apr. 1, 1985, abandoned.

[30] Foreign Application Priority Data

Apr. 3, 1984 [JP] Japan .................................. 59-65272

[51] Int. Cl.$^4$ ............................................ A61K 31/74
[52] U.S. Cl. ...................................................... 424/79
[58] Field of Search .......................................... 424/79

[56] References Cited

U.S. PATENT DOCUMENTS

| | | | |
|---|---|---|---|
| 4,107,098 | 8/1978 | Tamura et al. | 428/499 |
| 4,412,011 | 10/1983 | Kihara et al. | 424/79 |
| 4,557,930 | 12/1985 | Kihara et al. | 424/79 |

OTHER PUBLICATIONS

Chemical Abstracts, vol. 96 (1982) #205418w; Mitsubishi.
Patents Abstracts of Japan, vol. 9, No. 1 (C-259)[1724], Jan. 5th, 1985; & JP-A-59 155 421 (Mitsubishi Yuka K.K.) 04-09-1984.

*Primary Examiner*—Leonard Schenkman
*Assistant Examiner*—Joseph A. Lipovsky
*Attorney, Agent, or Firm*—Frishauf, Holtz, Goodman & Woodward

[57] ABSTRACT

There is disclosed a cholesterol level-lowering agent which comprises as a main component a strongly basic anion exchange resin having imidazolium salts as functional groups, said resin being a copolymer of (A) a high molecular quaternary salt and (B) a polyfunctional epoxy compound having two or more oxirane rings.

20 Claims, No Drawings

CHOLESTEROL LEVEL-LOWERING AGENTS

This application is a continuation of application Ser. No. 718,074, filed Apr. 1, 1985, now abandoned.

BACKGROUND OF THE INVENTION

This invention relates to an anticholesteremic agent or a cholesterol level-lowering agent and, more particularly, it is concerned with an anticholesteremic agent comprising as a main component a strongly basic anion exchange resin having imidazolium salts as functional groups.

It has already been known that an anion exchange resin is applicable as the so-called anticholesteremic agent for lowering a blood cholesterol level (U.S. Pat. Nos. 3,499,960 and 3,780,171 and British Pat. No. 929,391 and Japanese Patent Laid-Open Application No. 10386/1978). The mechanism that administration of an anion exchange resin could lower blood cholesterol may be considered as stated below. Namely, a basic anion exchange resin would adsorb and fix bile acids present in the intestine to prevent said bile acids from reabsorption and to promote conversion of cholesterol, which is equilibrated with bile acids in the liver, to bile acids, whereby blood cholesterol lowered.

A representative basic anion exchange resin, which has been hitherto applied as an anticholesteremic agent, is an ion exchange resin having aliphatic quarternary ammonium salts as functional groups (U.S. Pat. Nos. 3,499,960 and 3,780,171). However, such anion exchange resin has drawbacks of a large dosage (8 to 16 g/day) and difficulty in ingestion due to its low activity.

Also, the anion exchange resin having aliphatic quaternary ammonium salts as functional groups can be prepared by reacting an aliphatic tertiary amine with a haloalkyl group introduced onto a cross-linked polymer, but the resultant anion exchange resin bears an offensive odor characteristic of aliphatic amine and would not be put into practical use as such. Then, decrease in such offensive odor has been attempted practically by coating the surface of said anion exchange resin, but increase in dosage should be unavoidable due to a reduced ion exchange capacity caused by surface coating.

In order to solve these drawbacks, the present inventors had already developed an anticholesteremic agent using as a main component an anion exchange resin prepared by using imidazoles for forming an anion exchangeable group, as filed in Japanese Patent Laid-Open Application No. 24310/1982.

The above invention could overcome the prior difficulties, but a far higher active product has been desired.

Namely, the anion exchange resin of the above invention is prepared by reacting a halomethyloxirane compound with an imidazole and then reacting the resultant modified imidazole with a polyfunctional epoxy compound. However, said modified imidazole is a mixture of imidazole, 1:1 or 1:2 adduct of imidazole and halomethyloxirane compound, and an oligomer, and further is not separable so that the resultant anion exchange resin has a less content of the imidazolium salt capable of contributing to salt-splitting power among basic exchangeable groups upon imidazole and, though a higher activity can be seen as compared with the prior product, a far more highly active product has been desired.

SUMMARY OF THE INVENTION

An object of this invention is to provide an anticholesteremic agent having as a main component a strongly basic anion exchange resin having a higher adsorptivity of bile acids and no offensive odor.

The strongly basic anion exchange resin which may be employed as a main component for the present anticholesteremic or cholesterol level-lowering agent is such a strongly basic anion exchange resin having as functional groups imidazolium salts, said resin being a copolymer of:

(A) a high molecular quarternary salt having the following formula (I):

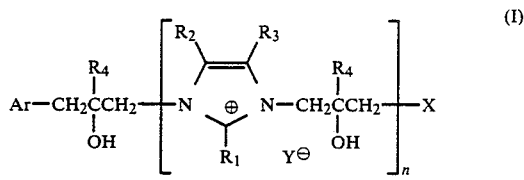

wherein $R_1$ is a hydrogen atom, an alkyl group of 1 to 17 carbon atoms or an aryl group of 6 to 8 carbon atoms, $R_2$ and $R_3$ may be the same or different and each represents a hydrogen atom or an alkyl group of 1 to 3 carbon atoms, $R_4$ is a hydrogen atom or a methyl group, a counter ion $Y^\ominus$ is a halide ion, a hydroxide ion or a ½ (sulfate) ion, and n is an integer of 1 or more;

Ar represents a residue represented by the formula:

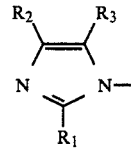

wherein $R_1$, $R_2$ and $R_3$ are as defined above, the formula:

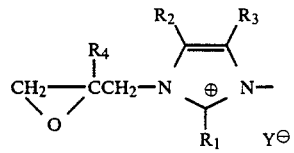

wherein $R_1$, $R_2$, $R_3$, $R_4$ and $Y^\ominus$ are as defined above, the formula:

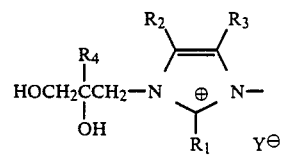

wherein $R_1$, $R_2$, $R_3$, $R_4$ and $Y^\ominus$ are as defined above or the formula:

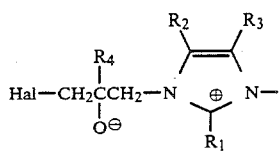

wherein $R_1$, $R_2$, $R_3$, $R_4$ and $Y^\ominus$ are as defined above and Ha is a halogen atom;

X represents a halogen atom or a residue represented by the formula:

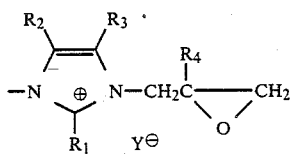

wherein $R_1$, $R_2$, $R_3$, $R_4$ and $Y^\ominus$ are as defined above or the formula:

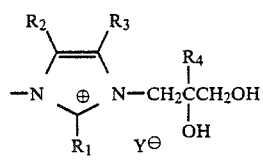

wherein $R_1$, $R_2$, $R_3$, $R_4$ and $Y^\ominus$ are as defined above. and (B) a polyfunctional epoxy compound having two or more oxirane rings.

DESCRIPTION OF THE PREFERRED EMBODIMENTS

In the above formula (I), as the alkyl group of 1 to 17 carbon atoms, there may be mentioned straight, branched or cyclic alkyl groups such as methyl, ethyl, n-propyl, isopropyl, n-butyl, isobutyl, tert-butyl, hexyl, cyclohexyl, undecyl, heptadecyl and so on; as the aryl group of 6 to 8 carbon atoms, there may be mentioned phenyl, tolyl, xylyl and so on; as the alkyl group of 1 to 3 carbon atoms, there may be mentioned methyl, ethyl, n-propyl, isopropyl, cyclopropyl and so on; as the halogen atom, there may be mentioned chlorine, bromine and so on.

The polyfunctional epoxy compound may be any of those having two or more oxirane rings and those with an epoxide equivalent of 100 to 3,000 are preferable. Illustrative examples of the above epoxy compound may include a bisphenol type epoxy resin, a polyglycol type epoxy resin, an alicyclic epoxy resin, a carboxylic acid type epoxy resin, an amine type epoxy resin, a novolak type epoxy resin and so on.

As the halogen ion, there may be mentioned a chloride ion, a bromide ion, an iodide ion and the like.

A molecular weight of the polymeric substance, which may constitute the strongly basic anion exchange resins as specified with these substituents, is not particularly critical if said polymeric substance is insoluble in water. Preferable strongly basic anion exchange resins of this invention are illustratively exemplified as shown in Table 1.

TABLE 1

| Sample | $R_1$ | $R_2$ | $R_3$ | $R_4$ | Polyfunctional epoxy compound | Counter ion |
|---|---|---|---|---|---|---|
| 1 | CH$_3$ | H | H | H | Epolite 100 MF | Cl$^-$ |
| 2 | CH$_3$ | H | " | " | Epolite 40 E | Cl$^-$ |
| 3 | C$_6$H$_5$ | H | " | " | Epikote 828 | SO$_4^-$ |
| 4 | C$_2$H$_5$ | CH$_3$ | " | " | Epolite 40 E | Cl$^-$ |
| 5 | H | H | " | " | Epolite 40 E | OH$^-$ |
| 6 | CH$_3$ | H | " | " | Epomate YH-434 | Cl$^-$ |
| 7 | CH$_3$ | H | " | " | (see structure below) | Cl$^-$ |
| 8 | CH$_3$ | H | " | " | (see structure below) | Cl$^-$ |

Sample 7 structure:

$$CH_2\text{-}CHCH_2-N \overset{\oplus}{\underset{CH_3\ Cl^-}{\phantom{X}}} N-CH_2CH-CH_2$$
(with oxirane rings on both ends)

Sample 8 structure:

$$CH_2\text{-}CHCH_2-\left[N \overset{\oplus}{\underset{CH_3\ Cl^-}{\phantom{X}}} N-CH_2CHCH_2\atop \underset{OH}{\phantom{X}}\right]_n N \overset{\oplus}{\underset{CH_3\ Cl^-}{\phantom{X}}} N-CH_2CH-CH_2$$

($n = 1 \sim 50$)

A particle diameter of the present strongly basic anion exchange resin is one which can be passed through 50 mesh (Tyler) and, in general, preferably of 50 to 325 mesh.

The strongly basic anion exchange resin having imidazolium salts as functional groups according to this invention may be prepared according to the process as disclosed in the co-pending Japanese Patent Application No. 28055/1983 for an improved process for preparing an anion exchange resin. More specifically, a halomethyloxirane compound is subjected to reaction with an imidazole to form a high molecular quaternary salt (intermediate) having imidazolium salts on a main chain and the resultant salt is resinified with a polyfunctional epoxy compound to produce the desired resin.

(1) Halomethyloxirane compounds
They are represented by the following formula:

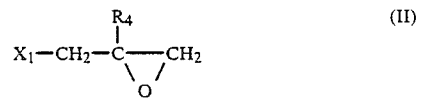

wherein $X_1$ is a halogen atom, particularly a chlorine, bromine or iodine atom and $R_4$ is as defined above.

Illustrative examples of this compound may include epichlorohydrin, epibromohydrin, β-methylepichlorohydrin and the like and they may be used in combination therewith.

(2) Imidazoles

They are represented by the following formula:

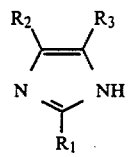

wherein $R_1$, $R_2$ and $R_3$ are as defined above.

Illustrative examples of these imidazoles are as recited below and they may be used in combination therewith. Namely, imidazole, 2-methylimidazole, 2-ethylimidazole, 2-n-propylimidazole, 2-isopropylimidazole, 2-undecylimidazole, 2-heptadecylimidazole, 2-phenylimidazole, 2,4-dimethylimidazole, 2-ethyl-4-methylimidazole, 2-phenyl-4-methylimidazole and the like.

(3) Preparation of high molecular quaternary salt (I)

Prepared by reaction of the halomethyloxirane compound having above formula (II) with the imidazole having above formula (III).

Reaction solvent may be any of those which would be inert to the above-mentioned reaction components and not prevent resinification with the under-mentioned polyfunctional epoxy compound, and water is particularly preferred for the preparation of a high molecular quaternary salt with a large molecular weight.

Reaction molar ratio is preferably 0.9 to 1.5 moles of the halomethyloxirane compound to 1 mole of the imidazole, more preferably 1 to 1.1 moles.

Reaction temperature is usually 30° to 150° C., and preferably 50° to 120° C. Reaction rate would be slow at less than 30° C., while, undesirably, side-reaction may apt to occur at more than 120° C.

Also, it is preferred to add dropwise the halomethyloxirane compound to the imidazole at 50° to 80° C. and, after completion of the dropwise addition, to raise a temperature to 80° to 120° C.

Reaction time is suitably 2 to 30 hours.

According to the above reactions, there can be obtained the high molecular quaternary salt (I) wherein Ar is

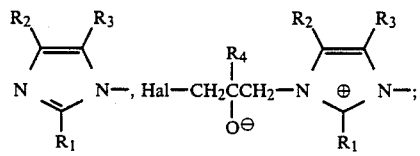

and X is Hal.

Further alkali treatment gives the salt (I) wherein Ar is

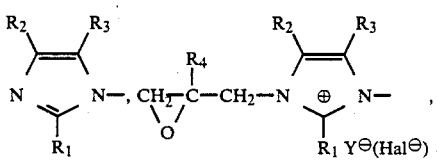

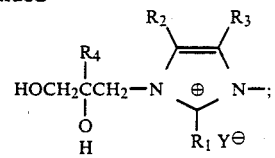

and X is

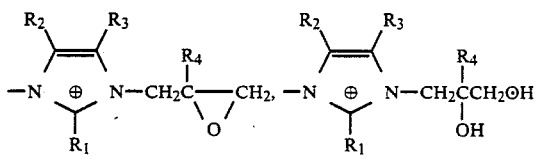

As the alkali treatment agent, there may be mentioned, for example, an alkali metal hydroxide such as NaOH, KOH and the like, an alkaline earth metal hydroxide such as Ca(OH)$_2$ and the like. An amount of the alkali treatment agent to be used is preferably 0.001 to 0.5 mole per mole of the halomethyloxirane compound, more preferably 0.01 to 0.3 mole. The agent is usually and preferably employed in a form of an aqueous solution thereof. Reaction temperature is usually 0° to 50° C. and preferably 10° to 25° C. Reaction time is suitably 1 to 5 hours.

In the high molecular quaternary salt obtained by using water as the reaction solvent and under the aforesaid conditions, n is the above formula (I) is not less than approximately 1, and usually 5 to 50.

(4) Polyfunctional epoxy compounds

The term "polyfunctional" is meant to indicate "having two or more oxirane rings".

A group of the polyfunctional epoxy compounds which may be employed in this invention is an epoxy resin having an epoxide equivalent of approximately 100 to 3,000 and illustratively includes the following: Bisphenol type epoxy resins (e.g., bisphenol A diglycidyl ether), polyglycol type epoxy resins (e.g., ethylene glycol diglycidyl ether, glycerine triglycidyl ether, trimethylol propane triglycidyl ether), alicyclic type epoxy resins (e.g., vinylcyclohexene diepoxide), carboxylic acid type epoxy resins (e.g., diglycidyl phthalate), amine type epoxy resins (e.g., N,N'-4,4'-diphenylmethane tetraglycidylamine, diglycidylaniline, diglycidyl compounds having imidazolium bases represented by the formula (IV):

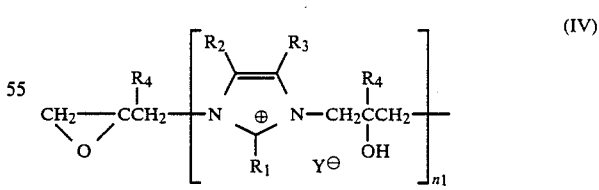

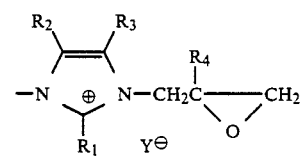

wherein $R_1$, $R_2$, $R_3$, $R_4$ and $Y^\ominus$ are as defined above and $n_1$ is an integer of 0 or more), novolak type epoxy resins (e.g., phenol novolak glycidyl ether), polyphenol type epoxy resins (e.g., tetrahydroxyphenylethane tetraglycidyl ether). They may be employed in combination therewith. Diglycidyl compounds having imidazolium bases represented by the above formula (IV) are synthesizable according to the process in which the high molecular quaternary salt prerared in the above (3) is reacted with a predetermined amount of a halomethyloxirane compound, followed by alkali treatment.

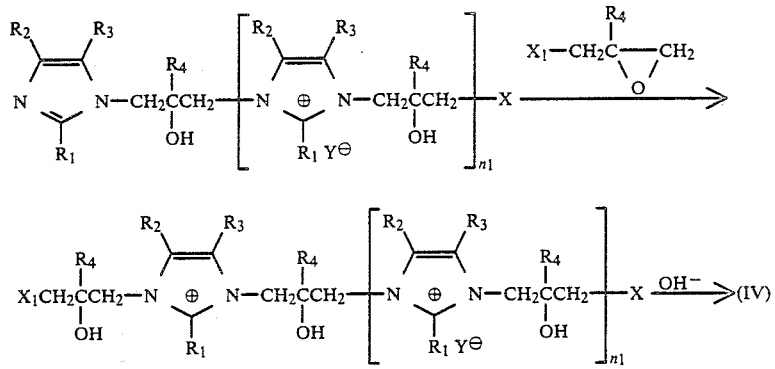

wherein $R_1$, $R_2$, $R_3$, $R_4$, $X$, $X_1$, $Y^\ominus$ and $n_1$ are as defined above.

(5) Resinification with polyfunctional epoxy compound

Heat curing reaction of the high molecular quaternary salt with the polyfunctional epoxy compound thus prepared can be carried out by blending both of them homogeneously at a predetermined ratio and then heating the resulting mixture. Generally, the polyfunctional epoxy compound is used in an amount of 10 to 70% by weight upon a total amount of the epoxy compound and the high molecular quaternary salt, preferably 20 to 60% by weight and heating is effected at 60° to 190° C., preferably 70° to 180° C. Heating period of time is about 3 to 15 hours. Heat cure may be effected in the presence of a diluent. As illustrative examples of the diluent, there may be mentioned any of the above-recited solvents (e.g., water).

Also, where the diglycidyl compound having imidazolium bases represented by the above formula (IV) is to be used as the polyfunctional epoxy compound, reaction of the high molecular quaternary salt prepared as above with a predetermined amount of the halomethyloxirane compound capable of reacting with a part of the former may be conducted, and then alkali treatment may be effected to accomplish synthesis of the aforesaid diglycidyl compound and admixture with the high molecular quaternary salt simultaneously. Then, resinification may be made by heating.

(6) Granulation of resulting strongly basic anion exchange resin

A resin mass of the strongly basic anion exchange resin prepared according to the above reaction is then granulated to a suitable particle size.

One of grinding means is grinding by means of a suitable grinding apparatus such as a ball mill and others.

As an alternative grinding means, there may be mentioned one utilizing characteristics of the present strongly basic anion exchange resin, i.e., self-degradation caused by hydration of the resin mass in a large volume of an aqueous medium. As the aqueous medium, there may be mentioned methanol, ethanol and others, in addition to water, and hydration temperature is about 20° to 100° C.

After granulation, the resultant product is washed with any of the above aqueous medium to remove soluble unreacted materials and then dried to afford the present strongly basic anion exchange resin in the form of granules.

The so-produced strongly basic anion exchange resin has the following characteristics;

salt-splitting capacity: 2.5 to 5.5 meq/g of dry resin
particle diameter: 50 to 325 mesh These various characteristics were measured according to the methods as described in the under-mentioned Preparation Example 1.

The present strongly basic anion exchange resin having imidazolium salts as functional groups has a higher content of the imidazolium base contribution to salt-splitting power, since the high molecular quaternary salt employed as a constituent component holds an extremely less contamination of a low molecular weight material as compared with the prior art product. Consequently, the resin shows a higher adsorption activity on bile acids, i.e., a stronger anticholesteremic activity. Also, the resin is less colored and odorless so that a very high usefulness for medicine is seen.

Then, acute toxicity of the present strongly basic anion exchange resin will be explained below.

A suspension of the resin in a 1% tragacanth gum solution as a dispersion medium was orally administered to ICR-JCL strain mice and $LD_{50}$ value was determined upon mortality after 1 week to show $LD_{50}$ value of above 5 g/kg.

A dosage of the present anticholesteremic agent may be 0.5 to 10 g daily for adults, preferably 1 to 4 g, because of a higher activity as compared with the prior art product, and the agent may usually be administered in 1 to 3 divided forms daily.

For administration of the present anticholesteremic agent to human beings, there may be normally used oral administration. For oral administration, one may ingest it before meals in the form of preparations such as tablet, fine granule, granule and others or may take it in a suspended form in water or other solutions.

Preparation Examples and Experiment Examples of this invention will be given below for illustrating this invention in greater detail and explaining effects of this invention.

PREPARATION EXAMPLE 1

(i) In a four-necked flask equipped with a reflux condenser, a thermometer and a stirrer were placed 72.4 g of 2-methylimidazole and a homogeneous solution was formed with 100 ml of water.

While reaction temperature was kept at 55° to 60° C., 81.6 g of epichlorohydrin were added dropwise with stirring over about 1 hour. Reaction temperature was raised to 90° C. and stirring was continued at that temperature over 14 hours to give a preparation solution of the high molecular quaternary salt (hereinafter referred to as "Intermediate A").

(ii) 63 parts of Intermediate A were homogeneously blended with 37 parts of a trifunctional epoxy compound "Epolite 100 MF" (manufactured by Kyoeisha Yushikagaku Kogyo Co., Ltd.) and then heat cure was effected at 80° C. for 3 hours and then at 170° C. for further 5 hours in the same manner as done in a conventional curing process of epoxy resins. The cured product was easily hydrated and decomposed by allowing it to be cooled and then left in water, thereby yielding a resinous and granular product. The resulting granular product was washed with ethanol and water to remove unreacted materials. Thereafter, heat drying was done and the resultant resin was ground by a ball mill.

The resulting strongly basic anion exchange resin (hereinafter referred to briefly as "CR-1") had the following characteristics;
 salt-splitting capacity: 3.9 meq/g
 particle diameter: 100 to 325 mesh The above characteristics were determined according to the under-mentioned methods.

Salt-splitting capacity: About 3 g of the resin are taken and immersed in 100 ml of a 1.0N-NaOH solution for 5 hours and then are washed with water up to neutral. After drying under reduced pressure, 2 to 3 g of the dried resin are precisely weighed (its weight is defined as A g), 100 ml of a 0.5N-NaCl solution are added thereto and the mixture is stirred for 4 hours and then left overnight. After suction-filtering, the filtrate is titrated with a 0.1N-HCl solution (a volume of the 0.1N-HCl solution required for titration in this instance is defined as B ml). Salt-splitting capacity is determined according to the following equation:

$$\text{salt-splitting capacity (meq/g)} = B \times (\text{titer of HC solution})/10A$$

Particle diameter: The dried resin was ground by means of a ball mill made by Alfred-Frisch Co., Ltd. over 1 to 2 hours. The ground resin was sieved to a given particle size by means of a magnetic, laboratory sieve shaker.

Characteristics of those strongly basic anion exchange resins as obtained in the following Preparation Examples were determined according to the above-mentioned measuring methods.

PREPARATION EXAMPLE 2

(i) 75 parts of Intermediate A prepared in Preparation Example 1-i) were blended homogeneously with 25 parts of a bifunctional epoxy compound, "Epolite 40 E" (manufactured by Kyoeisha Yushikagaku Kogyo Co., Ltd.) and then heat cure and post-treatment were carried out in the same manner as in Preparation Example 1-ii).

The resulting strongly basic anion exchange resin (hereinafter referred to briefly as "CR-2") had the following characteristics;
 salt-splitting capacity: 4.1 meq/g
 particle diameter: 100 to 325 mesh

PREPARATION EXAMPLE 3

(i) Following the same procedures as in Preparation Example 1-i) except that 63.5 g of 2-phenylimidazole and 40.8 g of epichlorohydrin were employed, there was obtained a preparation solution of a high molecular quaternary salt (hereinafter referred to as "Intermediate B").

(ii) 71 parts of Intermediate B were blended homogeneously with 29 parts of a bifunctional epoxy compound. "Epikote 828" (manufactured by Shell Chemical Co., Ltd.) and then heat cure and post-treatment were carried out in the same manner as in Preparation Example 1-ii).

The resulting strongly basic anion exchange resin (hereinafter referred to briefly as "CR-3") had the following characteristics;
 salt-splitting capacity: 2.7 meq/g
 particle diameter: 100 to 325 mesh

PREPARATION EXAMPLE 4

(i) Following the same procedures as in Preparation Example 1-i) except that 48.6 g of 2-ethyl-4-methylimidazole, 60 ml of water and 40.8 g of epichlorohydrin were employed, there was obtained a preparation solution of a high molecular quaternary salt (hereinafter referred to as "Intermediate C").

(ii) 70 parts of Intermediate C were blended homogeneously with 30 parts of a bifunctional epoxy compound, "Epolite 40 E" and then heat cure and post-treatment were carried out in the same manner as in Preparation Example 1-ii).

The resulting strongly basic anion exchange resin (hereinafter referred to briefly as "CR-4") had the following characteristics;
 salt-splitting capacity: 3.1 meq/g
 particle diameter: 100 to 325 mesh

PREPARATION EXAMPLE 5

(i) Following the same procedures as in Preparation Example 1-i) except that 30 g of imidazole, 30 ml of water and 40.8 g of epichlorohydrin were employed, there was obtained a preparation solution of a high molecular quaternary salt (hereinafter referred to as "Intermediate D").

(ii) 71 parts of Intermediate D were blended homogeneously with 29 parts of a bifunctional epoxy compound, "Epolite 40 E" and then heat cure and post-treatment were carried out in the same manner as in Preparation Example 1-ii).

The resulting strongly basic anion exchange resin (hereinfter referred to briefly as "CR-5") had the following characteristics;
 salt-splitting capacity: 4.1 meq/g
 particle diameter: 100 to 325 mesh

PREPARATION EXAMPLE 6

85 parts of Intermediate A prepared in Preparation Example 1-i) were blended homogeneously with 15 parts of a tetrafunctional epoxy compound, "Epomate YH-434" (manufactured by Toto Kasei Co., Ltd.) and then heat cure and post-treatment were carried out in the same manner as in Preparation Example 1-ii).

The resulting strongly basic anion exchange resin (hereinafter referred to briefly as "CR-6") had the following characteristics;
salt-splitting capacity: 4.6 meq/g
particle diameter: 100 to 325 mesh

PREPARATION EXAMPLE 7

80 parts of Intermediate A obtained in Preparation Example 1-i) were blended homogeneously with 20 parts of a bifunctional epoxy compound represented by the following formula (V):

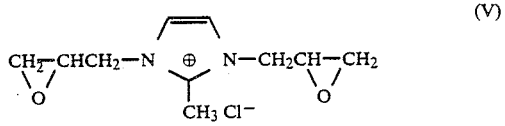

and then heat cure and post-treatment were carried out in the same manner as in Preparation Example 1-ii).

The resulting strongly basic anion exchange resin (hereinafter referred to briefly as "CR-7") had the following characteristics;
salt-splitting capacity: 4.9 meq/g
particle diameter: 100 to 325 mesh The bifunctional epoxy compound represented by the above-mentioned formula (V) was synthesized as follows:

(a) In a four-necked flask equipped with a reflux condenser, a thermometer and a stirrer were placed 24.6 g (0.3 mole) of 2-methylimidazole, and then 60 ml of water were added to form a homogeneous solution.

(b) While reaction temperature was kept at 25° to 30° C., 55.5 g (0.6 mole) of epichlorohydrin were added dropwise over 1 hour and stirring was continued for further 3 hours.

(c) After reaction temperature was brought to 0° to 5° C., 60 g of a 20% aqueous solution of sodium hydroxide (0.3 mole) were added dropwise over 1 hour. Stirring was continued at this temperature for 3 hours to give a preparation solution of the present epoxy compound.

PREPARATION EXAMPLE 8

(i) Following the same procedures as in Preparation Example 1-i) except that 41 g (0.5 mole) of 2-methylimidazole, 46.3 g (0.5 mole) of epichlorohydrin and 60 ml of water were employed, there was obtained a preparation solution of a high molecular quaternary salt (Intermediate A).

(ii) To a reaction mixture containing the high molecular quaternary salt as prepared hereinabove were addeddropwise, while keeping a temperature at 45° to 50° C. under stirring, 8.7 g (0.094 mole) of epichlorohydrin over 1 hour and reaction was continued at this temperature for further 2 hours.

(iii) After cooling to room temperature, 18.9 g (0.094 mole) of a 20% aqueous solution of sodium hydroxide were added dropwise over 15 minutes. After stirring at this temperature for further 2 hours, heat cure and post-treatment were carried out in the same manner as in Preparation Example 1-ii).

The resulting strongly basic anion exchange resin (hereinafter referred to briefly as "CR-8") had the following characteristics;
salt-splitting capacity: 5.0 meq/g
particle diameter: 100 to 325 mesh

EXPERIMENT EXAMPLE 1

Test in vitro (1) Adsorption test of sodium cholate with various strongly basic anion exchange resin, in vitro Into an Erlenmeyer flask were placed 30 ml of an aqueous solution of sodium cholate at a concentration of 2.58 mg/ml and each 30 mg of CR-1, CR-2, CR-3, CR-4, CR-5, CR-6, CR-7, CR-8 and cholestyramine was added thereto, respectively. After incubation at 37° C. for 6 hours, a supernatant was collected by centrifugation and the residual sodium cholate was quantitatively assayed according to an enzymatic reaction method [using a reagent for determining a concentration of bile acid, manufactured by Daiichi Kagaku Co., Ltd.) (Sterognost-3α-kit)]. The results are shown in Table-2.

TABLE 2

| | Proportion of combined sodium cholate (%) |
|---|---|
| Cholestyramine | 47 |
| CR-1 | 65 |
| CR-2 | 64 |
| CR-3 | 51 |
| CR-4 | 53 |
| CR-5 | 67 |
| CR-6 | 70 |
| CR-7 | 78 |
| CR-8 | 78 |

From the results shown in Table-2, it is apparent that the present strongly basic anion exchange resins, CR-1 to CR-8, can adsorb a large amount of sodium cholate.

(2) Adsorption test of various bile acid sodium salts, in vitro

In an Erlenmeyer flask were placed each 30 ml of an aqueous solution of bile acid sodium salts (sodium glycocholate, sodium taurocholate, sodium deoxycholate) at a concentration of 2.58 mg/ml and then each 30 mg of CR-1, CR-8 or cholestyramine were added thereto. Adsorption test was carried out according to the same method as in Experiment Example 1-1), to quantitatively assay residual bile acid sodium salts, respectively. The results are shown in Table-3.

TABLE 3

| Bile acid sodium salt | Proportion of combined bile acid sodium salts (%) | | |
|---|---|---|---|
| | Cholestyramine | CR-1 | CR-8 |
| Sodium glycocholate | 54 | 71 | 80 |
| Sodium taurocholate | 60 | 76 | 85 |
| Sodium deoxycholate | 60 | 84 | 91 |

From the results shown in Table-3, it is apparent that the present strongly basic anion exchange resin can also show a high adsorption activity on not only sodium cholate also the corresponding deoxy form (sodium deoxycholate), conjugated form with glycine (sodium glucocholate), conjugated form with taurine (sodium taurocholate) which are present in a large amount in vivo (in intestine).

EXPERIMENT EXAMPLE 2

Test for rats in vivo

Groups each consisting of 7 animals selected from Sprague-Dawley strain male rats weighing 175 to 180 g (6 weeks of age, Shizuoka Laboratory Animal Cooperative Union), were used for experiment. After pre-feeding for 1 week, the first group of rats was fed with only a high lipid diet [a powdery feed for rats containing 1% cholesterol and 0.5% bile powder (manufactured by Nippon Kurea Co., Ltd.)], while the 2nd to 4th, 5th to 7th and 8th to 10th groups of rats were orally administered forcibly once a day with, in addition to the above high lipid diet, suspensions in distilled water of cholestyramine (doses: 125, 250 and 500 mg/kg), CR-1 (doses: 125, 250 and 500 mg/kg) and CR-8 (doses: 125, 250 and 500 mg/kg), respectively. After 7 days from administration of the high lipid diet and the drug, blood samples were obtained from the tail vein of the rat and then a total cholesterol level in the centrifuged blood plasma was quantitatively determined by means of Cholesterol Test Wako Kit manufactured by Wako Pure Chemical Ind. Co., Ltd. The results are shown in Table-4.

From the results shown in Table-4, it is apparent that the present strongly basic anion exchange resins, CR-1 and CR-8 can exert an anticholesteremic activity or a cholesterol level-lowering activity in vivo.

TABLE 4

| | Dose (mg/kg) | Total cholesterol in blood plasma (mg/dl) | Inhibition ratio (%) |
|---|---|---|---|
| Control | — | 51 ± 2 | 100 |
| High lipid diet | — | 175 ± 15 | 0 |
| High lipid diet + cholestyramine | 125 | 160 ± 11 | 12.1 |
| High lipid diet + cholestyramine | 250 | 166 ± 10 | 7.3 |
| High lipid diet + cholestyramine | 500 | 138 ± 12** | 29.8 |
| High lipid diet + CR-1 | 125 | 124 ± 7*** | 41.1 |
| High lipid diet + CR-1 | 250 | 126 ± 8*** | 39.5 |
| High lipid diet + CR-1 | 500 | 111 ± 6*** | 51.6 |
| High lipid diet + CR-8 | 125 | 107 ± 6*** | 54.8 |
| High lipid diet + CR-8 | 250 | 118 ± 6*** | 46.0 |
| High lipid diet + CR-8 | 500 | 98 ± 7*** | 62.1 |

**$p < 0.01$
***$p < 0.001$

EXPERIMENT EXAMPLE 3

Test for rabbits in vivo (1) Groups each consisting of 7 animals selected from female New Zealand-White strain rabbits weighing 2.0–2.2 kg (4 months of age), were used for experiment.

After pre-feeding, rabbits were fed with a high lipid diet [a rabbit feed containing 0.67% cholesterol (manufactured by Oriental Yeast Co., Ltd.)] for 8 days, thereby providing hyperlipidemic rabbits. Rabbits having approximately similar levels of hyperlipidemia were selected and divided into groups.

The first group of rabbits was fed continuously with a high lipid diet solely, while the 2nd and 3rd groups and the 4th to 6th groups of rabbits were orally administered forcibly once a day with, in addition to the above high lipid diet, suspensions in distilled water of cholestyramine (doses: 125 and 500 mg/kg) and CR-8 (doses: 31.25, 125 and 500 mg/kg), respectively.

After 1, 2 and 3 weeks from administration of the high lipid diet and the drug, bood samples were obtained from the auris vein of the rabbit and a total cholesterol level in the centrifuged blood plasma was quantitatively determined by means of Cholesterol Test Wako Kit (manufactured by Wako Pure Chemical Ind. Co., Ltd.). The results are shown in Table-5a.

TABLE 5a

| | Dose (mg/kg) | Plasma cholesterol (mg/dl) | | |
|---|---|---|---|---|
| | | 1 week | 2 weeks | 3 weeks |
| High lipid diet | — | 493 ± 38 | 966 ± 63 | 1178 ± 122 |
| High lipid diet + cholestyramine | 125 | 493 ± 41 | 917 ± 64 | 1122 ± 98 |
| High lipid diet + cholestyramine | 500 | 494 ± 40 | 781 ± 60** | 843 ± 66*** |
| High lipid diet + CR-8 | 31.25 | 487 ± 40 | 862 ± 46 | 1095 ± 69 |
| High lipid diet + CR-8 | 125 | 489 ± 40 | 668 ± 51*** | 796 ± 71*** |
| High lipid diet + CR-8 | 500 | 493 ± 42 | 516 ± 63*** | 368 ± 58*** |

**$p < 0.01$
***$p < 0.001$ (2) An anion exchange resin prepared according to the method described in Preparation Example 1 of Japanese Patent Laid-Open Application No. 24310/1982 (hereinafter referred to as "CR-9") was tested in the same manner as in the above Experiment Example 3-1) and the results are shown in Table-5b.

TABLE 5b

| | Dose (mg/kg) | Plasma cholesterol (mg/dl) | | |
|---|---|---|---|---|
| | | 1 week | 2 weeks | 3 weeks |
| High lipid diet | — | 437 ± 33 | 850 ± 85 | 1138 ± 111 |
| High lipid diet + CR-9 | 250 | 435 ± 35 | 771 ± 60 | 1037 ± 66 |
| High lipid diet + CR-9 | 500 | 436 ± 36 | 625 ± 76 | 629 ± 75*** |

***$p < 0.001$ (3) Inhibition ratios were determined upon Tables-5a and -5b and the results are shown in Table-5c.

TABLE 5c

| | Dose (mg/kg) | Inhibition ratio (%) | |
|---|---|---|---|
| | | 2 weeks | 3 weeks |
| Cholestyramine | 125 | 10.4 | 8.2 |
| | 500 | 39.3 | 49.1 |
| CR-8 | 31.25 | 20.7 | 11.2 |
| | 125 | 62.2 | 55.2 |
| | 500 | 95.1 | 118.0 |
| CR-9 | 250 | 18.9 | 14.3 |
| | 500 | 54.2 | 72.4 |

From the results shown in Table-5c, it is apparent that the present strongly basic anion exchange resin (CR-8) shows a higher cholesterol level lowering activity, as compared with the prior art product (cholestyramine) and the resin disclosed in Japanese Patent Laid-Open Application No. 24310/1982 (CR-9), and also exerts a sufficient activity even at a lower dosage.

Therefore, a lowered dosage may be applicable with the present cholesterol level lowering agent, as compared with the prior art product.

We claim:

1. A cholesterol level-lowering agent which consists essentially of a strongly basic anion exchange resin having imidazolium salts as functional groups, said resin being a copolymer of:

(A) a high molecular quaternary salt having the following formula (I):

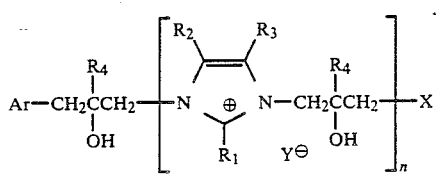

wherein $R_1$ is a hydrogen atom, an alkyl group of 1 to 17 carbon atoms or an aryl group of 6 to 8 carbon atoms, $R_2$ and $R_3$ may be the same or different and each represents a hydrogen atom or an alkyl group of 1 to 3 carbon atoms, $R_4$ is a hydrogen atom or a methyl group, a counter ion $Y^\ominus$ is a halide ion, a hydroxide ion or a ½ (sulfate) ion, and n is an integer of 1 or more;
Ar represents a residue represented by the formula:

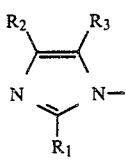

wherein $R_1$, $R_2$ and $R_3$ are as defined above, the formula:

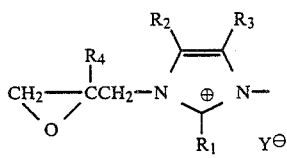

wherein $R_1$, $R_2$, $R_3$, $R_4$ and $Y^\ominus$ are as defined above,
the formula:

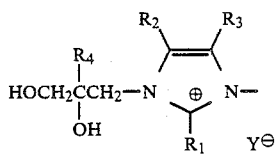

wherein $R_1$, $R_2$, $R_3$, $R_4$ and $Y^\ominus$ are as defined above or
the formula:

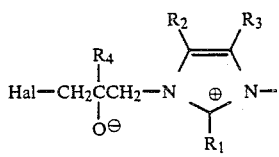

wherein $R_1$, $R_2$, $R_3$, $R_4$ and $Y^\ominus$ are as defined above and Hal is a halogen atom; and
X represents a halogen atom or a residue represented by the formula:

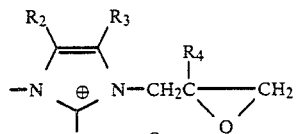

wherein $R_1$, $R_2$, $R_3$, $R_4$ and $Y^\ominus$ are as defined above or
the formula:

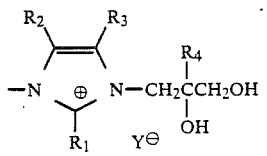

wherein $R_1$, $R_2$, $R_3$, $R_4$ and $Y^\ominus$ are as defined above,
and
(B) a polyfunctional epoxy compound having two or more oxirane rings and selected from the group consisting of diglycidyl compounds having imidazolium bases represented by the formula (IV):

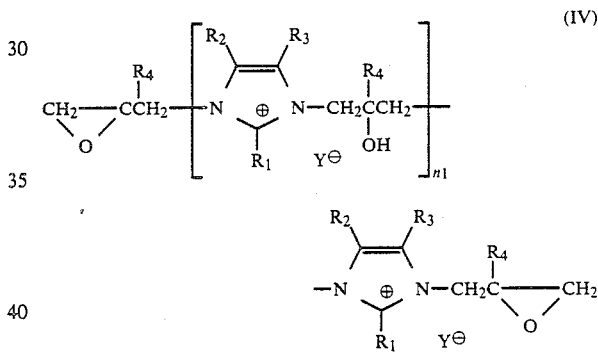

wherein $R_1$, $R_2$, $R_3$, $R_4$ and $Y^\ominus$ are as defined above and $n_1$ is an integer of 0 or more, and having an epoxide equivalent of 100 to 3,000.

2. The agent according to claim 1, wherein $R_1$ is a hydrogen atom, a methyl group or a phenyl group, $R_2$ is a hydrogen atom or a methyl group, and $R_3$ and $R_4$ are each a hydrogen atom in formula (I).

3. The agent according to claim 2, wherein $R_1$ is a methyl group, $R_2$, $R_3$ and $R_4$ are each a hydrogen atom in formula (I).

4. The agent according to claim 2, wherein $R_1$ is a phenyl group, and $R_2$, $R_3$ and $R_4$ are each a hydrogen atom in formula (I).

5. The agent according to claim 2, wherein $R_1$, $R_2$, $R_3$ and $R_4$ are each a hydrogen atom in formula (I).

6. The agent according to claim 1, wherein n is an integer of 5 to 50.

7. The agent according to claim 1, wherein the polyfunctional epoxy compound has an epoxide equivalent of 100 to 3,000 and is one selected from the group consisting of a bisphenol type epoxy resin, a polyglycol type epoxy resin, an alicyclic type epoxy resin, a carboxylic acid type epoxy resin, an amine type epoxy resin, a novolak type epoxy resin and a polyphenol type epoxy resin.

8. The agent according to claim 1, wherein said resin has salt-splitting capacity of 2.5 to 5.5 meq/g and a particle diameter of 50 to 325 mesh.

9. The agent according to claim 1, wherein $R_1$ is a methyl group and $R_2$, $R_3$ and $R_4$ are each a hydrogen atom, the counter ion $Y^\ominus$ is $Cl^-$ and n is an integer of 5 to 50 in formula (I); the diglycidyl compound has an epoxide equivalent of 100 to 3,000; and the resin has salt-splitting capacity of 2.5 to 5.5 meq/g and a particle diameter of 50 to 325 mesh.

10. The agent according to claim 1, wherein $R_1$ is a methyl group and $R_2$, $R_3$ and $R_4$ are each a hydrogen atom, the counter ion $Y^\ominus$ is $Cl^-$ and n is an integer of 5 to 50 in formula (I); and the resin has salt-splitting capacity of 2.5 to 5.5 meq/g and a particle diameter of 50 to 325 mesh.

11. A method of lowering the level of cholesterol in blood, which comprises administering to a human being an anticholesteremic amount of a composition consisting essentially of a strongly basic anion exchange resin having imidazole salts in combination with a pharmaceutically acceptable carrier, said resin being a copolymer of:

(A) a high molecular quaternary salt having the following formula (I):

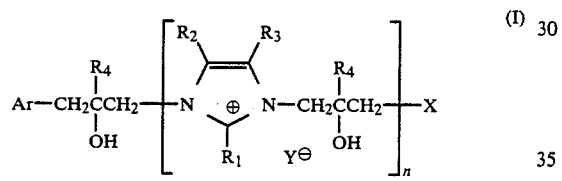

wherein $R_1$ is a hydrogen atom, an alkyl group of 1 to 17 carbon atoms or an aryl group of 6 to 8 carbon atoms, $R_2$ and $R_3$ may be the same or different and each represents a hydrogen atom or an alkyl group of 1 to 3 carbon atoms, $R_4$ is a hydrogen atom of a methyl group, a counter ion $Y^\ominus$ is a halide ion, a hydroxide ion or a ½ (sulfate) ion, and n is an integer of 1 or more;

Ar represents a residue represented by the formula:

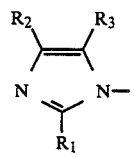

wherein $R_1$, $R_2$ and $R_3$ are as defined above, the formula:

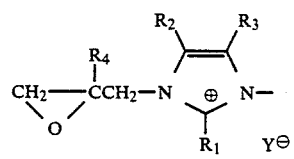

wherein $R_1$, $R_2$, $R_3$, $R_4$ and $Y^\ominus$ are as defined above, the formula:

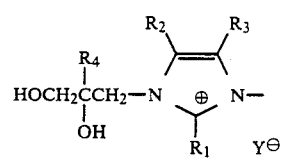

wherein $R_1$, $R_2$, $R_3$, $R_4$ and $Y^\ominus$ are as defined above or the formula:

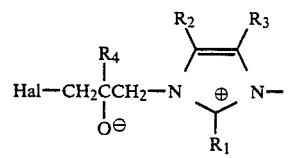

wherein $R_1$, $R_2$, $R_3$, $R_4$ and $Y^\ominus$ are as defined above and Hal is a halogen atom; and X represents a halogen atom or a residue represented by the formula:

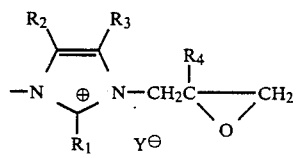

wherein $R_1$, $R_2$, $R_3$, $R_4$ and $Y^\ominus$ are as defined above or the formula:

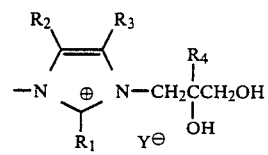

wherein $R_1$, $R_2$, $R_3$, $R_4$ and $Y^\ominus$ are as defined above.

and
(B) a polyfunctional epoxy compound having two or more oxirane rings and selected from the group consisting of diglycidyl compounds having imidazolium bases represented by the formula (IV):

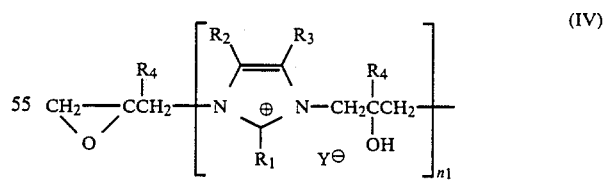

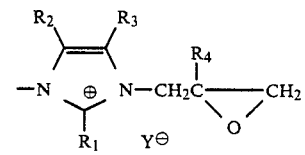

wherein $R_1$, $R_2$, $R_3$, $R_4$ and $Y^\ominus$ are as defined above and $n_1$ is an integer of 0 or more, and having an epoxide equivalent of 100 to 3,000.

12. The method according to claim 11, wherein $R_1$ is a hydrogen atom, a methyl group or a phenyl group, $R_2$ is a hydrogen atom or a methyl group, and $R_3$ and $R_4$ are each a hydrogen atom in formula (I).

13. The method according to claim 12, wherein $R_1$ is a methyl group, $R_2$, $R_3$ and $R_4$ are each a hydrogen atom in formula (I).

14. The method according to claim 12, wherein $R_1$ is a phenyl group, and $R_2$, $R_3$ and $R_4$ are each a hydrogen atom in formula (I).

15. The method according to claim 12, wherein $R_1$, $R_2$, $R_3$ and $R_4$ are each a hydrogen atom in formula (I).

16. The method according to claim 11, wherein n is an integer of 5 to 50.

17. The method according to claim 11, wherein the polyfunctional epoxy compound has an epoxide equivalent of 100 to 3,000 and is one selected from the group consisting of a bisphenol type epoxy resin, a polyglycol type epoxy resin, an alicyclic type epoxy resin, a carboxylic acid type epoxy resin, an amine type epoxy resin, a novolak type epoxy resin and a polyphenol type epoxy resin.

18. The method according to claim 11, wherein said resin has salt-splitting capacity of 2.5 to 5.5 meq/g and a particle diameter of 50 to 325 mesh.

19. The method according to claim 11, wherein $R_1$ is a methyl group and $R_2$, $R_3$ and $R_4$ are each a hydrogen atom, the counter ion $Y^\ominus$ is $Cl^-$ and n is an integer of 5 to 50 in formula (I); the polyfunctional epoxy compound is a trifunctional epoxy compound and has an epoxide equivalent of 100 to 3,000; and the resin has salt-splitting capacity of 2.5 to 5.5 meq/g and a particle diameter of 50 to 325 mesh.

20. The method according to claim 11, wherein $R_1$ is a methyl group and $R_2$, $R_3$ and $R_4$ are each a hydrogen atom, the counter ion $Y^\ominus$ is $Cl^-$ and n is an integer of 5 to 50 in formula (I); the polyfunctional epoxy compound is a diglycidyl compound having imidazolium bases represented by the formula (IV):

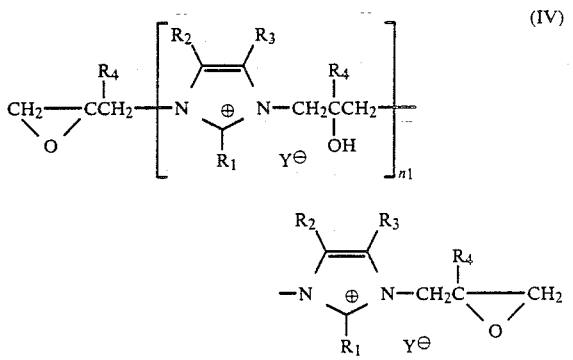

wherein $R_1$, $R_2$, $R_3$, $R_4$ and $Y^\ominus$ are as defined in claim 1 and $n_1$ is an integer of 0 or more, and has an epoxide equivalent of 100 to 3,000; and the resin has salt-splitting capacity of 2.5 to 5.5 meq/g and a particle diameter of 50 to 325 mesh.

* * * * *